· US005614508A

United States Patent [19]
Nikam

[11] Patent Number: 5,614,508
[45] Date of Patent: Mar. 25, 1997

[54] AMINO ACID DERIVATIVES OF SUBSTITUTED QUINOXALINE 2,3-DIONE DERIVATIVES AS GLUTAMATE RECEPTOR ANTAGONISTS

[75] Inventor: Sham Nikam, Ann Arbor, Mich.

[73] Assignee: Warner-Lambert Company, Morris Plains, N.J.

[21] Appl. No.: 474,878

[22] Filed: Jun. 7, 1995

[51] Int. Cl.$^6$ ...................... A61K 31/495; C07D 241/52
[52] U.S. Cl. ............................ 514/80; 514/249; 544/337; 544/354; 564/166
[58] Field of Search ...................... 514/80, 249; 544/337, 544/354; 564/166

[56] References Cited

U.S. PATENT DOCUMENTS

| | | | |
|---|---|---|---|
| 2,271,187 | 6/1981 | Atkinson et al. | 424/309 |
| 4,156,734 | 5/1979 | Stone | 424/273 R |
| 4,206,216 | 6/1980 | Atkinson et al. | 424/263 |

FOREIGN PATENT DOCUMENTS

| | | |
|---|---|---|
| 488959A2 | 6/1992 | European Pat. Off. |
| 0627434A1 | 12/1994 | European Pat. Off. |
| 6228112A | 5/1993 | Japan |
| WO-91/01724 | 2/1991 | WIPO |
| 93/08188 | 4/1993 | WIPO |
| 94/26747 | 11/1994 | WIPO |

OTHER PUBLICATIONS

Copending USSN 08/124,770.
Copending USSN 08/404,400.
C. Bigge, et al., *Current Opinion in Therapeutic Patents*, 1993, 951–989.
M. A. Rogawski, *TiPS*, 1993, 14:325–331.
H. Li, et al., *J of Cerebral Blood Flow & Metabolism*, 1993, 13:6, 933–939.
B. Nellgard, et al., *J of Cerebral Blood Flow & Metabolism*, 1992, 12:1, 2–11.
R. Bullock, et al., *J of Cerebral Blood Flow & Metabolism*, 1994, 14:3, 466–471.
D. Xue, et al., *J of Cerebral Blood Flow & Metabolism*, 1994, 14:2, 251–261.
X-j. Xu, et al., *J of Pharmacology & Experimental Therapeutics*, 1993, 267:1, 140–267.
T. Namba, et al., *Brain Research*, 1994, 638:36–44.
S. Browne, et al., *Brain Research*, 1994, 641:10–20.
S-i. Yamaguchi, et al., *Epilepsy Research*, 1993, 15:179–184.
S. E. Smith, et al., *European J of Pharmacology*, 1991, 201:179–183.
T. Klockgether, et al., *Annals of Neurology*, 1993, 34:4, 585–593.
P. T. Francis, et al., *J of Neurochemistry*, 1993, 60:5, 1589–1604.
S. A. Lipton, *TINS*, 1993, 16:12, 527–532.
S. A. Lipton, et al., *New England J of Medicine*, 1994, 330:9, 613–622.
C. F. Bigge, *Biochemical Pharmacology*, 1993, 45:8, 1547–1561.

*Primary Examiner*—Matthew V. Grumbling
*Attorney, Agent, or Firm*—Elizabeth M. Anderson

[57] ABSTRACT

A novel series of substituted quinoxaline 2,3-diones useful as neuroprotective agents are taught. Novel intermediates, processes of preparation, and pharmaceutical compositions containing the compounds are also taught. The compounds are glutamate antagonists and are useful in the treatment of stroke, cerebral ischemia, or cerebral infarction resulting from thromboembolic or hemorrhagic stroke, cerebral vasospasms, hypoglycemia, cardiac arrest, status epilepticus, perinatal asphyxia, anoxia, Alzheimer's, Parkinson's, and Huntington's diseases.

14 Claims, No Drawings

AMINO ACID DERIVATIVES OF SUBSTITUTED QUINOXALINE 2,3-DIONE DERIVATIVES AS GLUTAMATE RECEPTOR ANTAGONISTS

BACKGROUND OF THE INVENTION

This invention is for novel glutamate receptor antagonists which are new compounds of the 5,6,7,8-substituted quinoxaline 2,3-dione type. The fused ring system is substituted at the a- or b-position by amino acid derivatives. The compounds are active as excitatory amino acid receptor antagonists acting at glutamate receptors, including either or both N-methyl-D-aspartate (NMDA) receptors and non-NMDA receptors such as the α-amino-3-hydroxy-5-methyl-4-isoxazole propionic acid (AMPA) receptor and the kainate receptor. The invention also relates to the use of those quinoxaline-2,3-diones as neuroprotective agents for treating conditions such as cerebral ischemia or cerebral infarction resulting from a range of phenomena, such as thromboembolic or hemorrhagic stroke, cerebral vasospasms, hypoglycemia, cardiac arrest, status epilepticus, perinatal asphyxia, anoxia such as from drowning, pulmonary surgery, and cerebral trauma, as well as to treat chronic neurodegenerative disorders such as Alzheimer's Disease, Parkinsonism and Huntington's Disease, and as anticonvulsants. The compounds of the present invention may also be useful in the treatment of schizophrenia, epilepsy, anxiety, pain and drug addiction. Excessive excitation by neurotransmitters can cause the degeneration and death of neurons. It is believed that this degeneration is in part mediated by the excitotoxic actions of the excitatory amino acids (EAA) glutamate and aspartate at the N-methyl-D-aspartate (NMDA) receptor, the α-amino- 3-hydroxy-5-methyl-4-isoxazole propionic acid (AMPA) receptor, and the kainate receptor. AMPA/kainate receptors may be referred to jointly as non-NMDA receptors. This excitotoxic action is considered responsible for the loss of neurons in cerebrovascular disorders such as cerebral ischemia or cerebral infarction resulting from a range of conditions, such as thromboembolic or hemorrhagic stroke, cerebral vasospasm, hypoglycemia, cardiac arrest, status epilepticus, perinatal asphyxia, anoxia such as from drowning, pulmonary surgery, and cerebral trauma, as well as lathyrism, Alzheimer's Disease, Parkinson's Disease, and Huntington's Disease.

Several classes of quinoxalinedione derivatives have been disclosed as glutamate (EAA) receptor antagonists. For example, among excitatory amino acid receptor antagonists recognized for usefulness in the treatment of disorders are those that block AMPA receptors (Bigge C. F. and Malone T. C., *Curr. Opin. Ther. Pat.*, 1993:951; Rogawski M. A., *TiPS*, 1993;14:325). AMPA receptor antagonists have prevented neuronal injury in several models of global cerebral ischemia (Li H. and Buchan A. M., *J. Cerebr. Blood Flow Metab.*, 1993;13:933; Nellgard B. and Wieloch T., *J. Cerebr. Blood Flow Metab.*, 1992;12:2) and focal cerebral ischemia (Bullock R., Graham D. I., Swanson S., McCulloch J., *J. Cerebr, Blood Flow Metab.*, 1994;14:466; Xue D., Huang Z.-G., Barnes K., Lesiuk H. J., Smith K. E., Buchan A. M., *J. Cerebr. Blood Flow Metab.*, 1994;14:251). AMPA antagonists have also shown efficacy in models for analgesia (Xu X.-J., Hao J.-X, Seiger A., Wiesenfeld-Hallin Z., *J. Pharmacol. Exp. Ther.*, 1993;267:140), and epilepsy (Namba T., Morimoto K., Sato K., Yamada N., Kuroda S., *Brain Res.*, 1994;638:36; Brown S. E., McCulloch J., *Brain Res.*, 1994;641:10; Yamaguchi S. I., Donevan S. D., Rogawski M. A., *Epilepsy Res.*, 1993;15:179; Smith S. E., Durmuller N., Meldrum B. S., *Eur, J, Pharmacol.*, 1991;201:179). AMPA receptor antagonists have also demonstrated promise in chronic neurodegenerative disorders such as Parkinsonism (Klockgether T., Turski L., Honoré T., Zhang Z., Gash D. M., Kurlan R., Greenamyre J. T., *Ann. Neurol.*, 1993;34(4):585–593).

Excitatory amino acid receptor antagonists that block NMDA receptors are also recognized for usefulness in the treatment of disorders. NMDA receptors are intimately involved in the phenomenon of excitotoxicity, which may be a critical determinant of outcome of several neurological disorders. Disorders known to be responsive to blockade of the NMDA receptor include acute cerebral ischemia (stroke or cerebral trauma, for example), muscular spasm, convulsive disorders, neuropathic pain, and anxiety, and may be a significant causal factor in chronic neurodegenerative disorders such as Parkinson's disease (Klockgether T., Turski L., *Ann. Neurol.*, 1993;34:585–593), human immunodeficiency virus (HIV) related neuronal injury, amyotrophic lateral sclerosis (ALS), Alzheimer's disease (Francis P. T., Sims N. R., Procter A. W., Bowen D. M., *J. Neurochem.*, 1993;60(5):1589–1604), and Huntington's disease. (See Lipton S., *TINS*, 1993;16(12):527–532; Lipton S. A., Rosenberg P. A., *New Eng. J. Med.*, 1994;330(9):613–622; and Bigge C. F., *Biochem. Pharmacol.*, 1993;45:1547–1561 and references cited therein.) NMDA receptor antagonists may also be used to prevent tolerance to opiate analgesia or to help control withdrawal symptoms from addictive drugs (Eur. Pat. Appl. 488,959A).

Copending U.S. Ser. No. 08/124,770 discloses glutamate receptor antagonist quinoxalinedione derivatives represented by the formula:

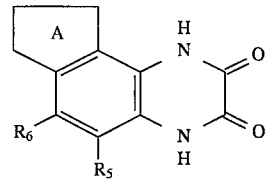

wherein A is a 5 to 7 atom containing ring having a nitrogen which may be substituted by hydrogen, alkyl, or $CH_2CH_2OH$. This application does not disclose or suggest compounds having the instant amino as substituents, or the requisite methodology to prepare the same.

Copending application U.S. Ser. No. 08/404,400 teaches glutamate receptor antagonists which are quinoxalinediones of formula

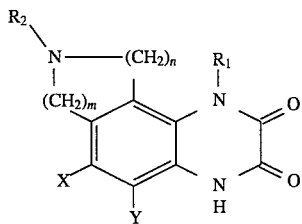

or a pharmaceutically acceptable salt thereof wherein $R^1$ is hydrogen, an alkyl, or an alkylaryl;

X and Y are independently hydrogen, halogen, nitro, cyano, trifluoromethyl, COOH, $CONR_4R^5$, $SO_2CF_3$, $SO_2R^4$, $SONR^4R^5$, alkyl, alkenyl, $(CH_2)_zCONR^4R^5$, $(CH_2)_zCOOR^4$, or $NHCOR^4$, wherein $R^4$ and $R^5$ are independently hydrogen, alkyl having 1 to 6 carbon atoms, cycloalkyl, or alkylaryl, and z is an integer from 0 to 4;

R² is alkylCOOR³, alkylamine, alkylquanidine, aryl, alkylaryl, COalkyl, COalkylaryl, CONR³alkyl, CONR³aryl, CONR³alkylaryl, CSNR³alkyl, CSNR³alkylaryl or a common amino acid moiety joined by an amide bond, wherein R³ is hydrogen, alkyl, or alkylaryl; and m and n are independently 0, 1, or 2 provided that m+n is >1.

This application does not disclose or suggest the compounds of the instant invention having amines as substituents at the a- or b-positions nor the methodology to prepare them.

JP06228112-A discloses glutamate receptor antagonists which are quinoxaline-2,3(1H,4H)-dione derivatives of formula

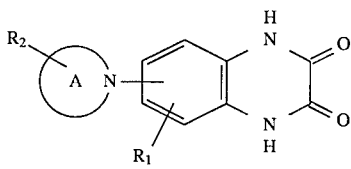

wherein $R^1$ is H, $NO_2$, or $CF_3$;

Ring A is a nitrogen-containing saturated heterocyclic group which may contain sulfur or oxygen;

$R^2$ is H, OH, lower alkoxy, COOH, lower alkoxy carbonyl, $NH_2$, or lower alkoxy, carbonyl-amino. This reference does not teach or suggest the instant compounds which must be attached to the quinoxaline dione fused ring system by an alkylene.

WO 93/08188 covers a tricyclic quinoxalinedione of formula

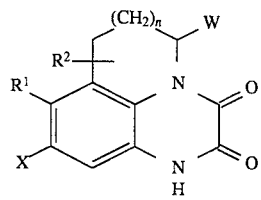

as useful or selective antagonists of glutamate receptors.

European Patent Application 0627434 covers tricyclic quinoxalinedione of Formula I below which are selective antagonists of glycine binding site of the NMDA receptor

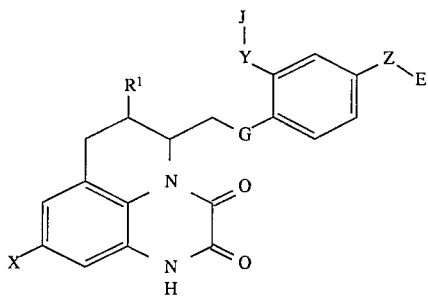

wherein

X represents hydrogen, alkyl, halogen, cyano, trifluoromethyl, or nitro;

$R^1$ represents hydrogen, alkyl, cycloalkyl, or cycloalkylalkyl;

G represents —CONR²— or —NR²CO—, wherein R² represents hydrogen or alkyl;

J represents an acidic group or a group which is convertible thereto in vivo;

E represents a basic group or a group which is convertible thereto in vivo;

Y represents a single bond, alkylene, alkenylene, substituted alkylene, or $Y^1$—Q—$Y^2$, wherein $Y^1$ represents a single bond or alkylene, $Y^2$ represents alkylene, and Q represents a heteroatom selected from oxygen or sulfur; and Z represents alkylene.

WO 94/26747 discloses compounds of Formula I below as useful in the treatment of cerebrovascular disorder

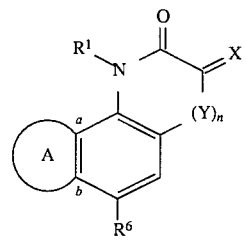

wherein $R^1$ is hydrogen, alkyl or benzyl;

X is O or $NOR^2$, wherein $R^2$ is hydrogen, alkyl, or benzyl;

Y is N—$R^4$, wherein $R^4$ is hydrogen, OH, or alkyl;

n is 0 or 1;

$R^6$ is phenyl, naphthyl, thienyl, pyridyl, all of which may be substituted one or more times with substituents selected from the group consisting of halogen;

$CF_3$, $NO_2$, amino, alkyl, alkoxy, and phenyl; and

A is a ring of 5 to 7 atoms fused with the benzo ring at the positions marked a and b.

The compounds of the instant invention differ from the art in that they provide noncoplanar compounds with greater solubility and, therefore, better ability to penetrate the blood-brain barrier. These are important attributes in pharmaceuticals.

An object of this invention is to provide novel quinoxalinediones with amines at the a- or b-position which function as antagonists.

SUMMARY OF THE INVENTION

The present invention is directed to compounds represented by Formula I:

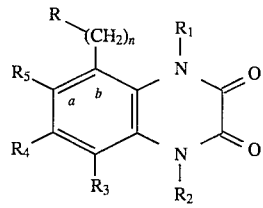

or a pharmaceutically acceptable salt thereof wherein R, $R_1$, $R_2$, $R_3$, $R_4$, $R_5$, and n are as described below.

The instant invention is also related to a pharmaceutical composition containing the compound defined by Formula I in an amount effective to treat cerebrovascular disorders responsive to the blockade of glutamate receptors (such as the α-amino-3-hydroxy-5-methyl-4-isoxazole propionic acid (AMPA) receptor and the kainate receptor), and a pharmaceutically acceptable carrier. Exemplary disorders responsive to such treatment include cerebral ischemia caused by cerebral trauma, stroke, hypoglycemia, heart attack, and surgery; anxiety and schizophrenia; and chronic neurodegenerative disorders such as Huntington's disease, ALS, Parkinsonism, and Alzheimer's disease. The pharmaceutical composition of this invention may also be employed as an analgesic or the treatment of epilepsy.

The invention further relates to a method of treating cerebrovascular disorders responsive to antagonism of glutamate receptors NMDA by administering a compound of above-defined Formula I in a unit dosage form.

Another object of this invention is to provide a method of treating disorders responsive to the antagonism of glutamate or aspartate receptors in a human by administering a pharmaceutically effective amount of the 2,3-quinoxalinediones of this invention.

Another object of this invention is to provide novel methods of preparing the 2,3-quinoxalinediones.

A further object of this invention is directed to novel intermediates useful in the preparation of the 2,3-quinoxalinediones of this invention.

DETAILED DESCRIPTION OF THE INVENTION

The substituted quinoxaline-2,3-diones of the instant invention are those of Formula I

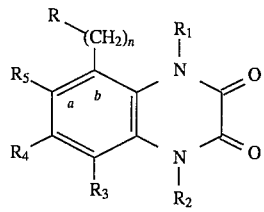

or a pharmaceutically acceptable salt thereof wherein

R is an amino acid derivative;

n is an integer of from 1 to 4;

$R_1$ is hydrogen, alkyl, aralkyl, carboxyalkyl, phosphoroalkyl, or phosphonoalkyl;

$R_2$ is hydrogen, hydroxy, or amino;

$R_3$ and $R_4$ are each independently hydrogen, alkyl, cycloalkyl, alkenyl, halogen, haloalkyl, nitro, cyano, $SO_2CF_3$, $C(O)R_6$ wherein $R_6$ is hydroxy, alkoxy,

alkyl, haloalkyl, aryl, aralkyl, $CH_2SO_2R_6$, $(CH_2)_mCO_2R_9$ wherein $R_9$ is hydrogen, alkyl, aralkyl, or cycloalkyl, $(CH_2)_mCONR_7R_8$, $(CH_2)_mSO_2NR_7R_8$, or $NHCOR_6$ wherein m is an integer of from 0 to 4 and $R_7$ and $R_8$ are each independently selected from hydrogen, alkyl, cycloalkyl, haloalkyl, or aralkyl; $R_5$ is hydrogen, alkyl, alkenyl, alkynyl, cycloalkyl, halogen, haloalkyl, aryl, heteroaralkyl, aralkyl, heteroaryl, nitro, cyano, trifluoromethylsulfonyl, $C(O)R_6$, $(CH_2)_mCO_2R_9$, $(CH_2)_mCONR_7R_8$, $SONR_7R_8$, or $NHCOR_6$ wherein m is as defined above and $R_7$ and $R_8$ are each independently hydrogen, alkyl, cycloalkyl, or aralkyl; and $R_5$ may be at the b-position and R—$(CH_2)_n$— at the a-position on the ring.

Preferred compounds are those of Formula I wherein

R is

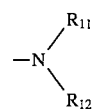

wherein $R_{11}$ is hydrogen, alkyl, or aralkyl, and $R_{12}$ is an amino acid of formula

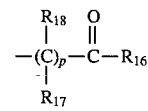

wherein p is an integer of from 1 to 5 and $R_{17}$ and $R_{18}$ are each independently on any carbon in —(C)p— and wherein $R_{16}$ is hydroxy, alkoxy, $NR_{19}R_{20}$ wherein $R_{19}$ and $R_{20}$ are each independently hydrogen, alkyl, cycloalkyl, or aralkyl, and $R_{17}$ and $R_{18}$ are independently selected from hydrogen, alkyl, cycloalkyl, heterocycloalkyl, aryl, aralkyl, heteroaralkyl, carboxyalkyl, aminoalkyl, thioalkyl, or hydroxyalkyl;

$R_1$ is hydrogen, alkyl, aralkyl, carboxyalkyl, phosphoroalkyl, or phosphonoalkyl;

$R_2$ is hydrogen, hydroxy, or amino;

$R_3$ and $R_4$ are each independently hydrogen, alkyl, cycloalkyl, alkenyl, halogen, haloalkyl, nitro, cyano, $SO_2CF_3$, $C(O)R_6$, $CH_2SO_2R_6$, $(CH_2)_nCO_2R_9$, $(CH_2)_nCONR_7R_8$, $(CH_2)_nSO_2NR_7R_8$, or $NHCOR_6$ wherein n is an integer of from 0 to 4 and $R_6$ as defined earlier, $R_7$, and $R_8$ are each independently selected from hydrogen, alkyl, cycloalkyl, or aralkyl, and $R_5$ is hydrogen, alkyl, alkenyl, alkynyl, cycloalkyl, halogen, haloalkyl, aryl, aralkyl, heteroaryl, nitro, cyano, $SO_2CF_3$, $C(O)R_6$ wherein $R_6$ is hydroxy, alkoxy,

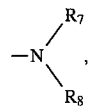

alkyl, haloalkyl, aryl, or aralkyl, $(CH_2)_mCO_2R_9$, $(CH_2)_mCONR_7R_8$, $SONR_9R_{10}$, or $NHCOR_6$ wherein m is as defined above and $R_7$ and $R_8$ are each independently hydrogen, alkyl, cycloalkyl, or aralkyl; and $R_5$ may also be at the b-position and R—$(CH_2)_n$— at the a-position on the ring.

Still more preferred are those of Formula I wherein R is

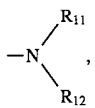

wherein $R_{11}$ is hydrogen or methyl, wherein $R_{12}$ is

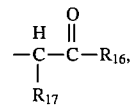

wherein $R_{16}$ is hydroxy, alkoxy, or amide, and $R_{17}$ is hydrogen, alkyl, cycloalkyl, heterocycloalkyl, aryl, aralkyl, heteroaralkyl, carboxyalkyl, aminoalkyl, thioalkyl, or hydroxyalkyl;

R$_1$ is hydrogen;

R$_2$ is hydrogen;

R$_3$ and R$_4$ are each independently hydrogen, halogen, or nitro;

R$_5$ is hydrogen, alkyl, or alkenyl.

Most preferred are selected from

[(7-Bromo-2,3-dioxo-6-vinyl-1,2,3,4-tetrahydro-quinoxalin-5-ylmethyl)-methyl-amino]-acetic acid;

[(7-Bromo-6-ethyl-2,3-dioxo-1,2,3,4-tetrahydro-quinoxalin-5-ylmethyl)-methyl-amino]-acetic acid;

[(6-Ethyl-7-nitro-2,3-dioxo-1,2,3,4-tetrahydro-quinoxalin-5-ylmethyl)-methyl-amino]-acetic acid ethyl ester; and

[(6-Ethyl-2,3-dioxo-1,2,3,4-tetrahydro-quinoxalin-5ylmethyl)-methyl-amino]-acetic acid.

The compounds of Formula I are capable of further forming both pharmaceutically acceptable acid addition salts. These forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *Journal of Pharmaceutical Science,* 1977;66:1–19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention may exist as a mixture of cis and trans isomers or as the individual cis and trans isomers or as R and S stereoisomers. The mixture of isomers as well as the individual isomers are intended to be encompassed within the scope of the present invention.

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "carboxyalkyl" means alkyl as above and attached to a carboxy group.

The term "phosphoroalkyl" means alkyl as above and attached to a phosphoro group.

The term "phosphonoalkyl" means alkyl as above and attached to a phosphonyl group.

The term "alkenyl" means a straight or branched unsaturated hydrocarbon radical having from 3 to 6 carbon atoms and includes, for example, 2-propenyl, 1-butenyl, 2-butenyl, 1-pentenyl, 2-pentenyl, 3-methyl-3-butenyl, 1-hexenyl, 2-hexenyl, 3-hexenyl, and the like.

"Alkynyl" means a straight or branched unsaturated hydrocarbon radical having from 2 to 6 carbon atoms and includes but is not limited to ethynyl, 2,3-propynyl, 1,2-propynyl, and 3,4-butynyl.

"Alkoxy" is O-alkyl of from 1 to 6 carbon atoms as defined above for "alkyl".

The term "aryl" means a monocyclic or bicyclic carbocyclic aromatic radical which is a phenyl or naphthyl group, substituted by 1 to 4 substituents selected from alkyl as defined above, alkoxy as defined above, thioalkoxy as defined above, hydroxy, halogen, trifluoromethyl, haloalkyl, amino, alkylamino as defined above for alkyl, dialkylamino as defined for alkyl, or 1,3-benzodioxol-5-yl.

The term "aralkyl" means aryl and alkyl as defined above and includes but is not limited to benzyl, 2-phenylethyl, 3-phenylpropyl; a preferred group is benzyl.

The term "heteroaryl" means a heteroaromatic radical such as but not limited to 2-, 3-, or 4-pyridinyl, 2-, 4-, or 5-pyrimidinyl, or 2-, 3-thienyl, isoquinolines, quinolines, imidazolines, pyrroles, indoles, and thiazoles.

"Halogen" is fluorine, chlorine, bromine, or iodine.

The term "haloalkyl" means halogen and alkyl as defined above such as but not limited to trifluoromethyl and trichloromethyl.

"Alkylaryl" means aryl as defined above and alkyl as defined above, for example, but not limited to benzyl, 2-phenylethyl, 3-phenylpropyl; a preferred group is benzyl.

The term "heterocycloalkyl" means an alicyclic ring with one or more atoms substituted by a heteroatom, for example, N, O, and S.

Common amino acid moiety means the naturally occurring α-amino acids, unnatural amino acids, substituted β, γ, δ amino acids and their enantiomers.

Common amino acids are: Alanine, β-alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

Modified and unusual amino acids are as would occur to a skilled chemist and are, for example, but not limited to:

10,11-Dihydro-5H-dibenzo[a,d]cyclohepten-5-yl)glycine or α-Amino-10,11-dihydro-5H-dibenzo[a,d]cycloheptene-5-acetic acid (Para-phenyl)phenylalanine, 3,3-Diphenylalanine, 3-Hydroxyproline, 4-Hydroxyproline, N-Methylphenylalanine, N-Methylaspartic acid, N-Methylisoleucine, N-Methylvaline, Norvaline, Norleucine, Ornithine, 2-Aminobutyric acid, 2-Amino-4-pentanoic acid (Allylglycine), N$^G$-nitroarginine, 2-Amino-3-(2-amino-5-thiazole)propanoic acid, 2-Amino-3-cyclopropanepropanoic acid (Cyclopropylalanine), Cyclohexylalanine (Hexahydrophenylalanine),
N-Methylcyclohexylalanine (N-Methylhexahydro phenylalanine),
2-Amino-4,4(RS)-epoxy-4-pentanoic acid,
$N^{im}$-2,4-Dinitrophenylhistidine,
2-Aminoadipic acid,
2-Amino-5-phenylpentanoic acid (Homophenyl alanine),
Methionine sulfoxide,
Methionine sulfone,
3-(1'-Naphthyl)alanine,
3-(2'-Naphthyl)alanine,
2-Amino-3-cyanopropanoic acid (Cyanoalanine),
Phenylglycine,
2-Aminopentanoic acid (Propylglycine),
2-Amino-6-(1-pyrrolo)-hexanoic acid,
2-Amino-3-(3-pyridyl)-propanoic acid (3-Pyridylalanine),
1,2,3,4-Tetrahydro-3-isoquinolinecarboxylic acid,
2-Amino-3-(4-thiazolyl)-propanoic acid,
O-tertiary butyl-tyrosine,
O-Methyl-tyrosine,
O-Ethyl-tyrosine,
$N^{in}$-Formyl-tryptophan,
5H-Dibenzo[a,d]cycloheptene glycine,
9H-Thioxanthene glycine, and
9H-Xanthene glycine.

The compounds of the invention exhibit valuable biological properties because of their strong excitatory amino acid (EAA) antagonizing properties at one of several binding sites on glutamate receptors: the AMPA ((RS)-amino-3-hydroxy-5-methyl-4-isoxazole propionic acid (or kainic acid) binding site on AMPA (non-NMDA) receptors or the glycine site of NMDA receptors.

The compounds of the present invention exhibit binding affinity for the AMPA receptors measured as described in Honoré T., et al., *Neuroscience Letters*, 1985;54:27–32. Preferred compounds demonstrate $IC_{50}$ values <100 µM in this assay. The compounds of the present invention exhibit binding affinity for the kainate site (non-NMDA receptor) measured as described in London E. D. and Coyle J., *Mol. Pharmacol.*, 1979;15:492. The compounds of the present invention exhibit binding affinity for the glycine site of the NMDA receptor measured as described in Jones S. M., et al., *Pharmacol. Methods*, 1989;21:161. To measure functional AMPA antagonist activity, the effects of the agent on AMPA-induced neuronal damage in primary cortical neuronal cultures was examined using techniques similar to those outlined by Koh J.-Y., et al., *J. Neurosci*, 1990;10:693. In addition, the neuronal damage produced by long-term exposure to 100 µM AMPA may be measured by the release of the cytosolic enzyme lactate dehydrogenase (LDH).

Selected compounds of the present invention were tested by one or more of the above-described assays. The data obtained in these assays is set forth in Table 1 below. The $IC_{50}$ values set forth in Table 1 are a measure of the concentration (µM) of the test substance which inhibits 50% of an induced release from the tested receptors.

TABLE 1

| Compound Number | Quinoxalinediones $IC_{50}$ µM | |
|---|---|---|
| | AMPA | KA |
| 1 | 1.76 | 4.68 |
| 2 | 2.35 | 6.72 |

TABLE 1-continued

| Compound Number | Quinoxalinediones $IC_{50}$ µM | |
|---|---|---|
| | AMPA | KA |
| 3 | 0.128 | 3.48 |
| 4 | 3.922 | 17.05 |

Additionally, a preliminary indicator of in vivo CNS activity related to anticonvulsant activity and potential neuroprotection, is a maximal electroshock assay in CF-1 strain mice (20–25 g) performed with corneal electrodes by conventional methods as described previously (Krall, et al., *Epilepsia*, 1988;19:409–428). The compounds of this invention generally demonstrate $ED_{50}$ values of <50 mg/kg.

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprises conventional ingredients in conventional proportions, with or without additional active compounds or principles, and such unit dosage forms may contain any suitable effective amount of the active ingredient commensurate with the intended daily dosage range to be employed. Tablets containing 10 mg of active ingredients or, more broadly, 0.1 to 100 mg per tablet, and accordingly suitable representative unit dosage forms.

Solid forms of pharmaceutical compositions for PO administration and injectable solutions are preferred.

The compounds of this invention are extremely useful in the treatment of central nervous system disorders related to their biological activity. The compounds of this invention may accordingly be administered to a subject, including a human, in need of treatment, alleviation, or elimination of an indication associated with the biological activity of the compounds. This includes especially excitatory amino-acid-dependent psychosis, excitatory amino-acid-dependent anoxia, excitatory amino-acid-dependent ischemia, excitatory amino-acid-dependent Parkinsonism, excitatory amino-acid-dependent convulsions, and excitatory amino-acid-dependent migraine. Suitable dosage ranges are 0.1 to 1000 mg daily, 10 to 50 mg daily, and especially 30 to 100 mg daily, dependent as usual upon the exact mode of administration, form in which administered, the indication toward which the administration is directed, the subject involved, and the body weight of the subject involved, and further, the preference and experience of the physician or veterinarian in charge.

The schemes and examples which follow are intended as an illustration of certain preferred embodiments of the invention, and no limitation of the invention is implied.

GENERAL SCHEME I

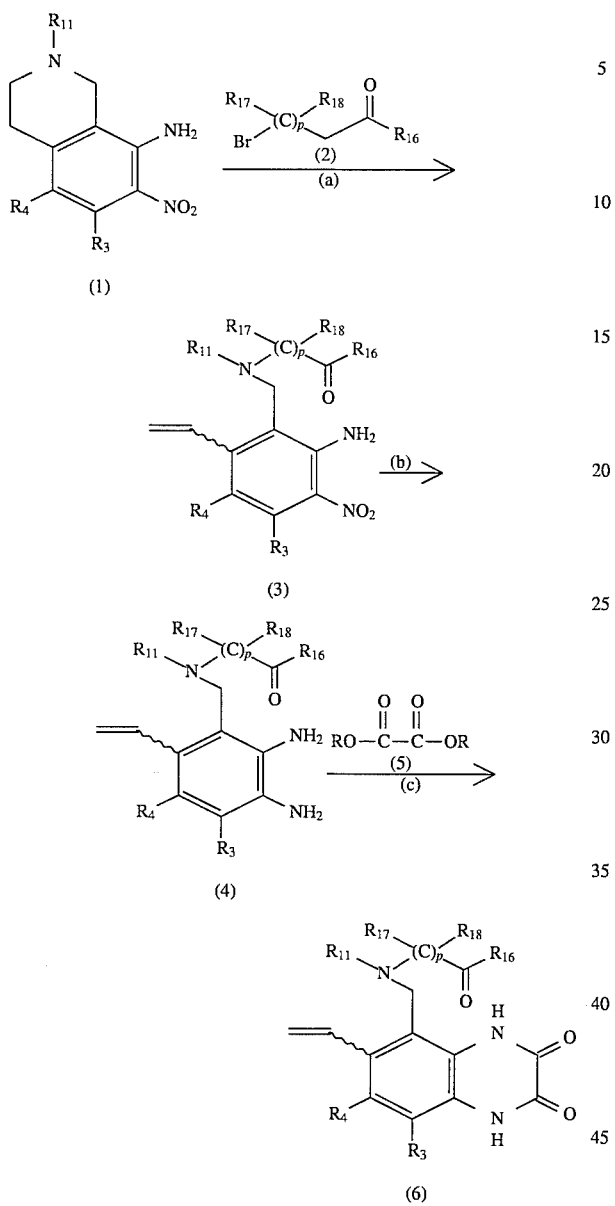

Scheme Ia

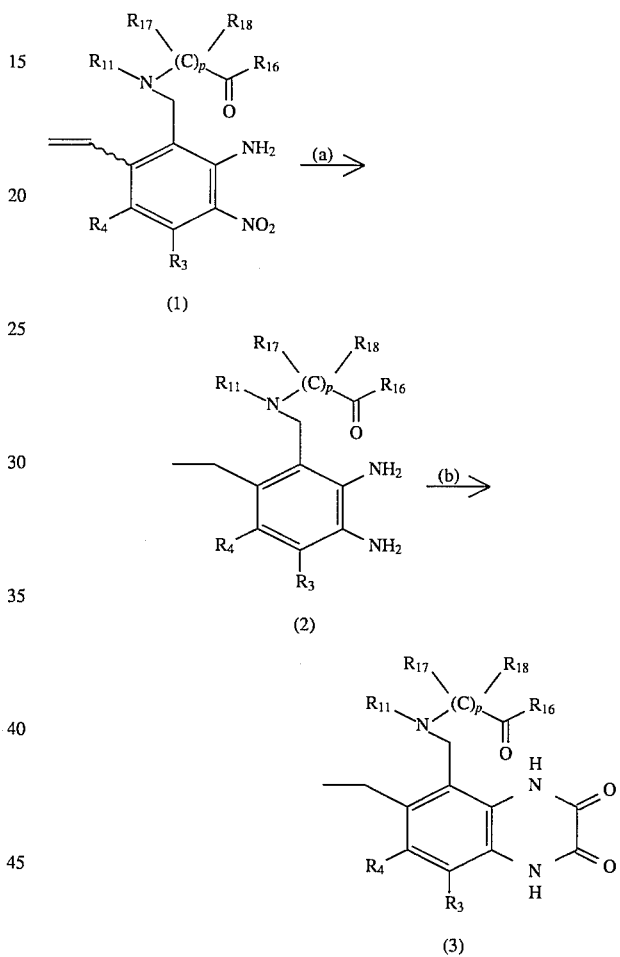

In Scheme I above, step (a) involves reacting appropriately substituted bromoacid derivative depicted in formula (2) with 5-bromo-2-methyl-7-nitro-1,2,3,4-tetrahydro-isoquinolin-8-yl amine depicted in formula (1) in ketone solvent like acetone, methylethylketone, or methylisobutylketone in the presence of an anhydrous base like potassium carbonate. The suspension is heated to the refluxing temperature of the solvent and stirred vigorously till TLC (SiO$_2$, pet. ether:EtOAc, 1:1) indicated completion. Solvent evaporated under reduced pressure and reaction is quenched with water. Product is extracted with ethyl acetate. Ethyl acetate extracts are washed with water and dried over MgSO$_4$. Product is purified by column chromatography (SiO$_2$, pet. ether:EtOAc, 95:5 to 75:25).

Step (b) involves selectively reducing the nitroaniline derivative depicted in formula (3) via hydrogenolysis (hydrogen gas around 50 psi) in the presence of a catalyst like Ra Ni in THF solution. Catalyst is filtered off and the filtrate evaporated and used for step (c) without further purification.

Step (c) involves reacting the o-phenylene diamine derivative depicted in formula (4) with appropriate oxalic acid derivative depicted in formula (5) wherein R is hydrogen or alkyl, for example, in an acidic solvent like HCl at elevated temperatures preferably around 80° C. The product is filtered and purified by crystallization.

In Scheme Ia above, step (a) involves selectively reducing the nitroaniline derivative depicted in formula (1) via hydrogenolysis (hydrogen gas around 50 psi) in the presence of a catalyst like Ra Ni in solution of hydroxylated solvents like methanol. Catalyst is filtered off and the mother liquor evaporated and the crude diamine shown in formula (2) is used further without additional purification.

Step (b) involves reacting the o-phenylene diamine derivative depicted in formula (2) with oxalic acid derivatives like dimethyl ester or ethylchlorooxalate preferably oxalic acid dihydrate in hydroxylated solvents preferably water in the presence of acids like hydrochloric acid. The final product (3) was obtained as a solid precipitating out of the reaction mixture.

Scheme 1

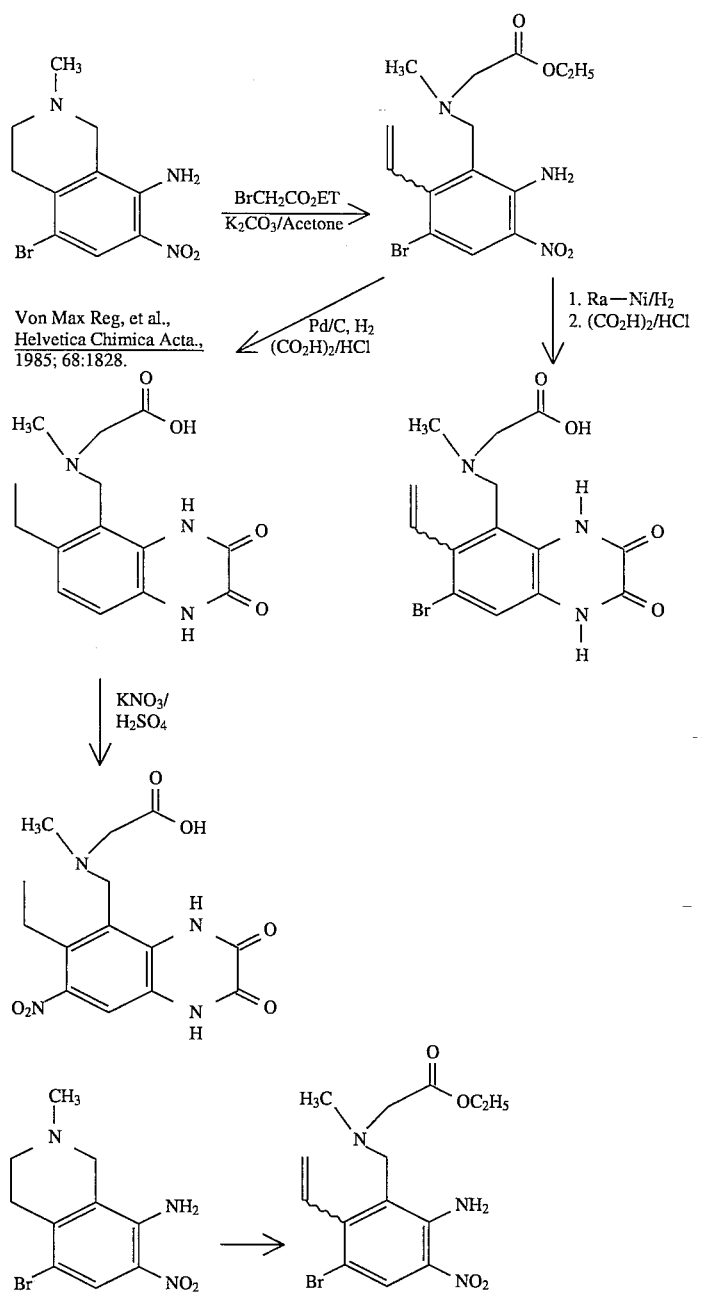

[(2-Amino-5-bromo-3-nitro-6-vinyl-benzyl)-methyl-amino]-acetic acid ethyl ester

To a suspension of 5-bromo-2-methyl-7-nitro-1,2,3,4-tetrahydro-isoquinolin-8-ylamine (2.86 g, mmol) and potassium carbonate (2.76 g, 20 mmol) in acetone (50 mL), ethyl bromoacetate (1.67 g, 10 mmol) was added. The reaction mixture was stirred under reflux until TLC ($SiO_2$, pet. ether:EtOAc, 1:1) indicated completion. Volatile materials were evaporated under vacuum and water (150 mL) was added to the yellow residue. Product was extracted with EtOAc (2×150 mL), and the EtOAc extracts were washed with water (2×50 mL) and dried over $MgSO_4$. Product was purified by chromatography ($SiO_2$, pet. ether:EtOAc, 95 to 75:25). Yield: 2.25 g, 60%, mp 68°–70° C.; MS (CI): M+1=373. CHN calculated for $C_{14}H_{18}BrN_3O_4$: C, 45.18; H, 4.87; N, 11.29. Found: C, 45.46; H, 4.95; N, 10.99.

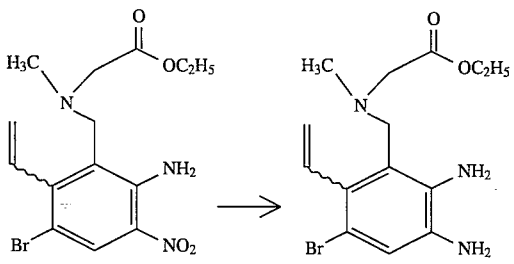

[(2,3-Diamino-5-bromo-6-vinyl-benzyl)-methyl-amino]-acetic acid ethyl ester

A suspension of [(2-amino-5-bromo-3-nitro-6-vinyl-benzyl)-methyl-amino]-acetic acid ethyl ester (0.5 g, 1.34 mmol) and Ra Ni (0.5 g) in THF (75 mL) was hydrogenated (H₂, 50 psi) in a Parr apparatus. Reaction mixture was filtered, and the filtrate was evaporated to give 0.45 g of the diamine, which was used further without purification. H-NMR (CDCl₃): 1.59 (t, 3H, J=7.2 Hz), 2.27 (s, 3H), 3.22 (s, 2H), 3.79 (s, 2H), 4.03 (bs, 2H), 4.18 (q, 2H), 5.14 (dd, 1H, J=1.8 Hz, J=16 Hz), 5.54 (dd, 1H, J=1.8 Hz, J=10 Hz), 6.59 (m, 1H), 6.93 (s, 1H).

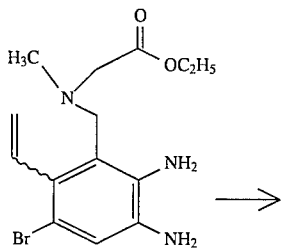
→
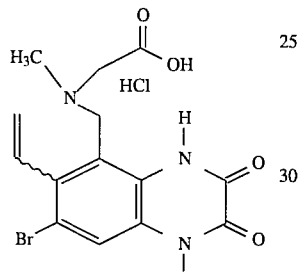

[(7-Bromo-6-vinyl-2,3-dioxo-1,2,3,4-tetrahydroquinoxalin-5-ylmethyl)-methylamino]-acetic acid hydrochloride A solution of [(2,3-diamino-5-bromo-6-vinyl-benzyl)-methyl-amino]-acetic acid ethyl ester (0.45 g) and oxalic acid (0.327 g, 2.6 mmol) in aqueous HCl (2N) was heated to 80° C. After 4 hours, reaction mixture was cooled and triturated with a spatula to give off-white precipitate, which was filtered and dried. Crystallized from water:acetone mixture. Yield: 0.162 g, mp >300° C. MS (CI): M+1=368. CHN calculated for C₁₄H₁₄BrN₃O₄.HCl: C, 41.56; H, 3.74; N, 10.38. Found: C, 41.5; H, 3.87; N, 10.05.

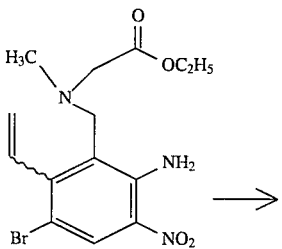
→
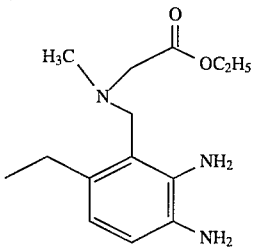

[(2,3-Diamino-6-ethyl-benzyl)-methyl-amino]-acetic acid ethyl ester

A solution of [(2-amino-5-bromo-3-nitro-6-vinyl-benzyl)-methyl-amino]-acetic acid ethyl ester (0.5 g, 1.34 mmol) and KOAc (0.13 g, 1.34 mmol) in EtOH was hydrogenated (H₂, 50 psi) over Pd/C (20%, 0.1 g) in a Parr apparatus. Reaction mixture was filtered and the filtrate evaporated on rotavapor to give a semisolid (0.42 g), which was used further without additional purification. HNMR (CDCl₃): 1.09 (t, 3H, J=7.4 Hz), 2.27 (s, 3H), 2.52 (q, 2H), 6.92 (s, 1H).

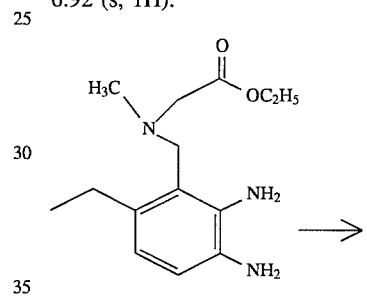
→
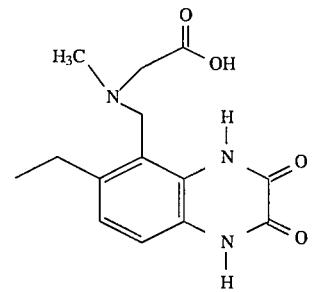

[(6-Ethyl-2,3-dioxo-1,2,3,4-tetrahydro-quinoxalin-5-ylmethyl)-methyl-amino]-acetic acid A solution of [2,3-diamino-6-ethyl-benzyl)-methyl-amino]-acetic acid ethyl ester (0.42 g) and oxalic acid dihydrate (0.327 g, 2.6 mmol) in aqueous HCl (2N, 20 mL) was heated to 90° C. Reaction mixture was stirred for 16 hours and cooled. Buff precipitate separated, which was filtered and air-dried, and used further without additional purification. Yield: 0.368 g, 84%. MS (CI): M+1=292.

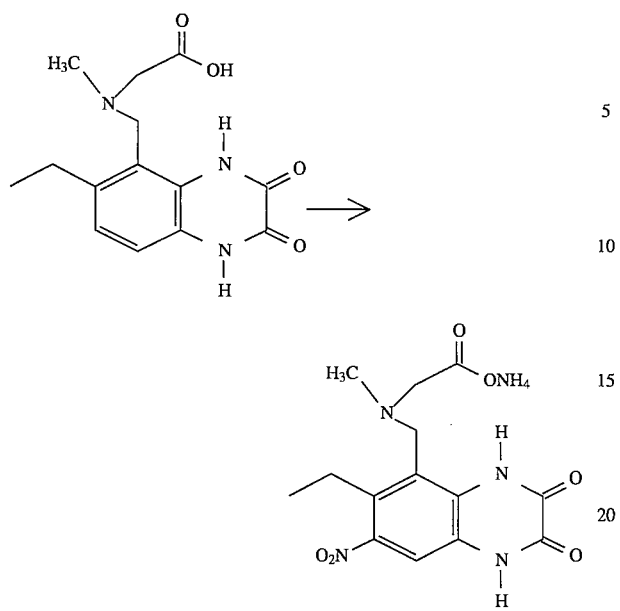

[(6-Ethyl-7-nitro-2,3-dioxo-1,2,3,4-tetrahydro-quinoxalin-5-ylmethyl)-methyl-amino]-acetic acid ammonium salt

[(6-Ethyl-2,3-dioxo-1,2,3,4-tetrahydro-quinoxalin-5-ylmethyl)-methyl-amino]-acetic acid (0.368 g) was dissolved in concentrated $H_2SO_4$ (5 mL). The dark solution was cooled to 0° C. and $KNO_3$ (0.5 g, 5 mmol) was added under stirring. Reaction mixture was allowed to warm to room temperature and quenched with ice after 12 hours. Pale brown residue was filtered, and the mother liquor was made basic by bubbling $NH_3$. Pale green precipitate was obtained, which was filtered and air dried. Yield: 0.100 g, 25.4%, mp >300° C. MS (CI): M+1=337.

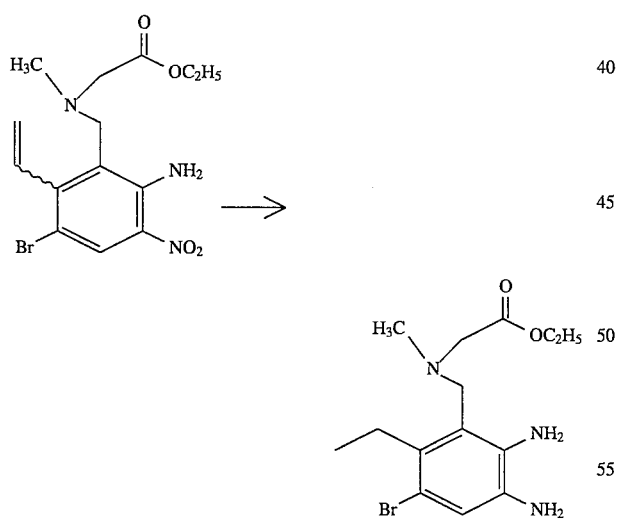

[(2,3-Diamino-5-bromo-6-ethyl-benzyl)-methyl-amino]-acetic acid ethyl ester

A solution of [(2-amino-5-bromo-3-nitro-6-vinyl-benzyl)-methyl-amino]-acetic acid methyl ester (0.475 g, 1.27 mmol) in EtOH (75 mL) was hydrogenated ($H_2$, 50 psi) in the presence of Ra Ni (0.2 g). Solvent was evaporated to give a white product, 0.450 g, which was used further without purification.

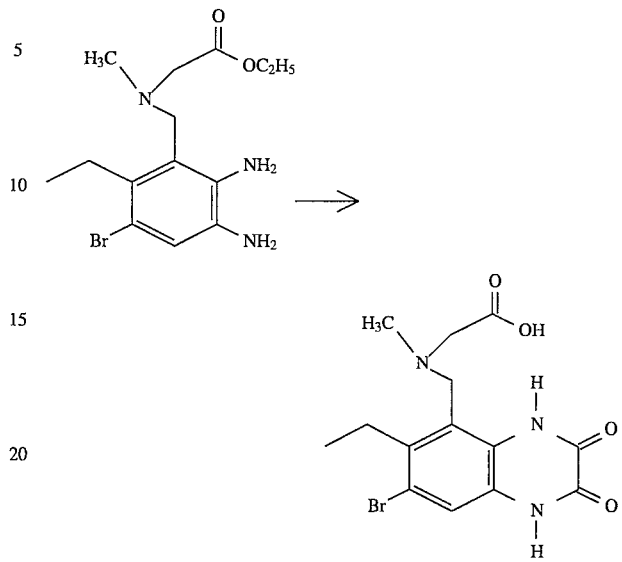

[(7-Bromo-6-ethyl-2,3-dioxo-1,2,3,4-tetrahydro-quinoxalin-5-ylmethyl)-methylamino]-acetic acid To a solution of [(2,3-diamino-5-bromo-6-ethyl-benzyl)-methyl-amino]-acetic acid ethyl ester (0.450 g) in HCl (5N, 5 mL), oxalic acid dihydrate (0.327 g, 2.6 mmol) was added under stirring. The reaction mixture was heated to 90° C. for 16 hours after which additional oxalic acid dihydrate (.163 g, 1.3 mmol) was added. On cooling after 2 hours, white precipitate (0.037 g) separated which was an impurity. On further cooling off-white solid separated, which was filtered and washed with water and methanol and dried. Yield:, 0.174 g, 34%, mp >245°–248° C. MS (CI): M—$CO_2H$+1= 326 (—$CO_2H$). $^1$H-NMR $CDCl_3$: (δ ppm) 1.15 (t, 3H, J=8.5 Hz), 2.84 (s, 3H), 3.11 (q, 2H), 4.32 (s, 2H), 4.71 (s, 2H, $D_2O$-exchanged), 7.56 (s, 1H).

GENERAL SCHEME II

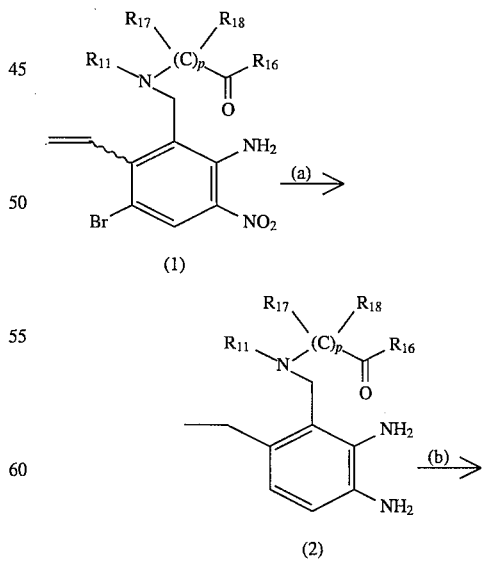

-continued
GENERAL SCHEME II

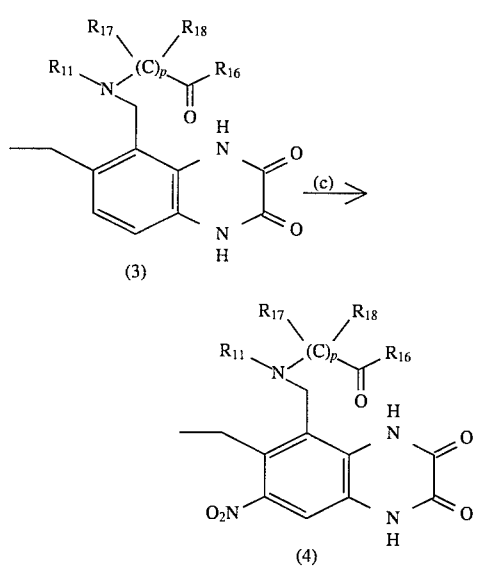

In Scheme II above, step (a) involves reducing the nitroaniline derivative depicted in formula (1) via hydrogenolysis (hydrogen gas around 50 psi) in the presence of a catalyst Pd/C in a solution of an hydroxylated solvent like ethanol. The reaction was filtered, and the filtrate was evaporated to give the crude o-phenylene diamine shown in formula (2), which is used further without additional purification.

Step (b) involves reacting the o-phenylene diamine derivative shown in formula (2) with oxalic acid derivative, preferably oxalic acid dihydrate in the presence of acid like hydrochloric acid in a solution of hydroxylated solvent preferably water. The reaction mixture is heated to temperatures around boiling, preferably 90° C. for about 16 hours. Product (3) precipitated from the reaction mixture on cooling and filtered and air-dried.

Step (c) involves reacting the quinoxaline 2,3-dione derivative shown in formula (3) with nitrating agents, preferably potassium nitrate in acidic solvents like TFA or sulfuric acid at temperatures around 0° C. The reaction mixture was poured in ice-water and filtered. The filtrate was neutralized with ammonia to give the desired product shown in formula (4).

Scheme IIa

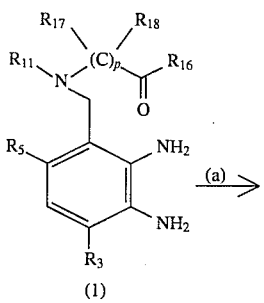

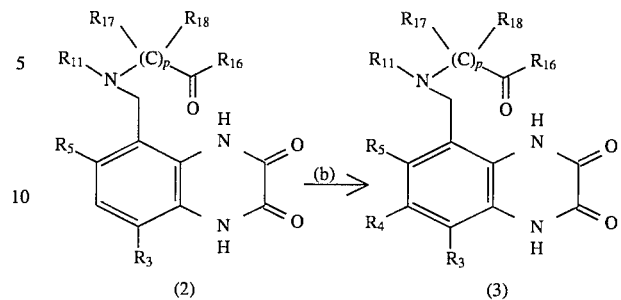

In Scheme IIa above, step (a) involves reacting the o-phenylenediamine derivative shown in formula (1) with an α-dicarbonyl compound, preferably dimethyl oxalate in a hydroxylated solvent like methanol. The reaction is carried out at elevated temperatures, preferably at the reflux for 4 to 20 hours, preferably hours. The product isolated by partial evaporation of the reaction mixture and filtering the precipitate and further purified by crystallization.

Step (b) involves electrophilic aromatic substitution of the quinoxaline 2,3-dione derivative shown in scheme (2), preferably nitration using nitrating mixtures like potassium nitrate/sulfuric acid or $HNO_3/Ac_2O$, preferably potassium nitrate/sulfuric acid at 0° C. to room temperature. Reaction mixture stirred for about 3 to 8 hours at room temperature and poured over ice. The solid separated was filtered. If no solid separated, the filtrate was neutralized with a base, preferably ammonia, to give the product.

Scheme 2

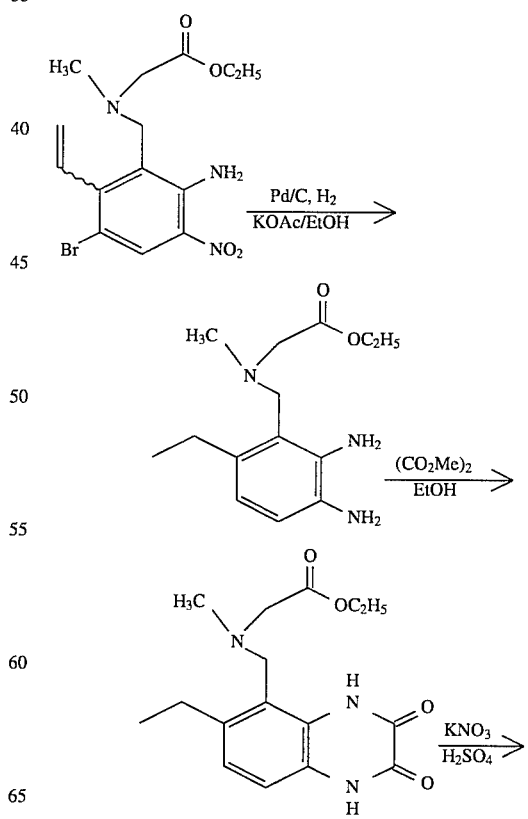

-continued
Scheme 2

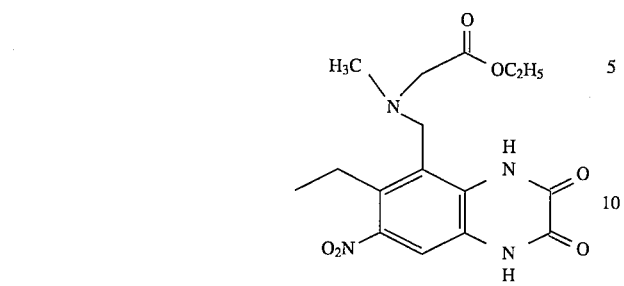

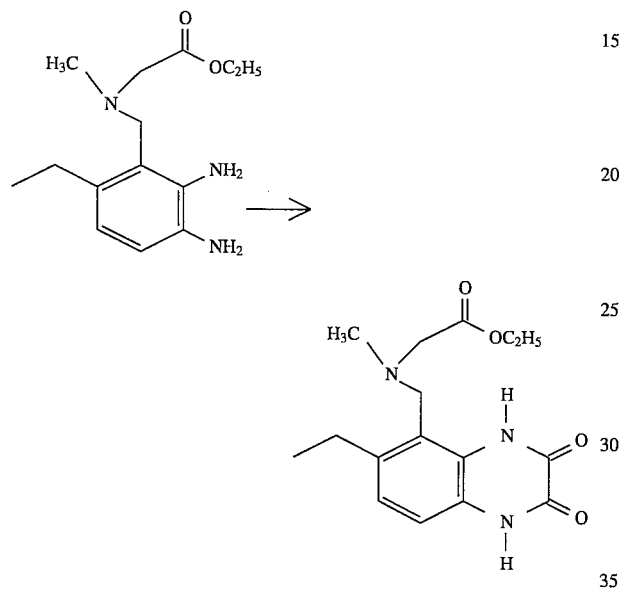

[(6-Ethyl-2,3-dioxo-1,2,3,4-tetrahydro-quinoxalin-5-ylmethyl)-methyl-amino]-acetic acid ethyl ester A solution of [(2,3-diamino-6-ethyl-benzyl)-methyl-amino]-acetic acid ethyl ester (0.57 g, 1.9 mmol) and dimethyl oxalate (0.472 g, 4 mmol) in EtOH (5 mL) was heated to reflux for 16 hours. Solvent was partially evaporated, and the reaction mixture was cooled. Buff precipitate was obtained 0.828 g. The product was purified by column chromatography (SiO$_2$, pet. ether:EtOAc, 95:5 to 75:25). Yield: 0.274 g, 45%. MS (CI): M+1=320. CHN calculated for C$_{16}$H$_{21}$N$_3$O$_4$: C, 60.18; H, 6.63; N, 13.16. Found: C, 59.87, H, 6.63, H, 12.74.

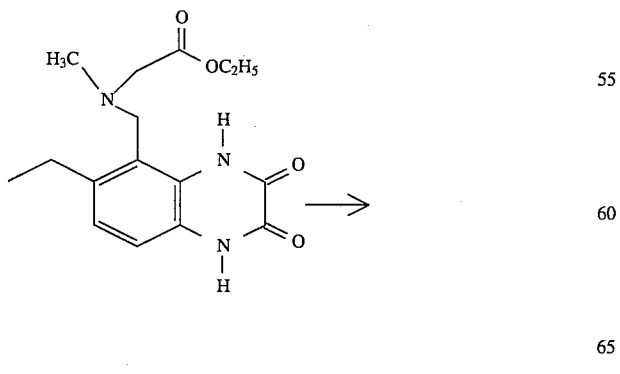

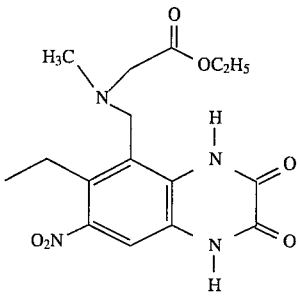

[(6-Ethyl-7-nitro-2,3-dioxo-1,2,3,4-tetrahydro-quinoxalin-5-ylmethyl)-methyl-amino]-acetic acid ethyl ester To a solution of [(6-ethyl-2,3-dioxo-1,2,3,4-tetrahydro-quinoxalin-5-ylmethyl)-methyl-amino]-acetic acid ethyl ester (0.175 g, 0.57 mmol) in concentrated H$_2$SO$_4$ (2 mL), KNO$_3$ (0.071 g, 0.71 mmol) was added under stirring at 0° C. Reaction mixture was stirred for hours and poured over ice. Brown precipitate was filtered, washed with water and dried. Product purified by column chromatography (SiO$_2$, CHCl$_3$:MeOH, 95 to 80:20). Yield: 0.135 g, 65%, mp 110° C. (effervescence), 185° C. MS (CI): M+1=365. CHN calculated for C$_{16}$H$_{20}$N$_4$O$_6$: C, 52.74; H, 5.53; N, 15.38. Found: C, 52.98; H, 5.48; N, 15.0.

GENERAL SCHEME II

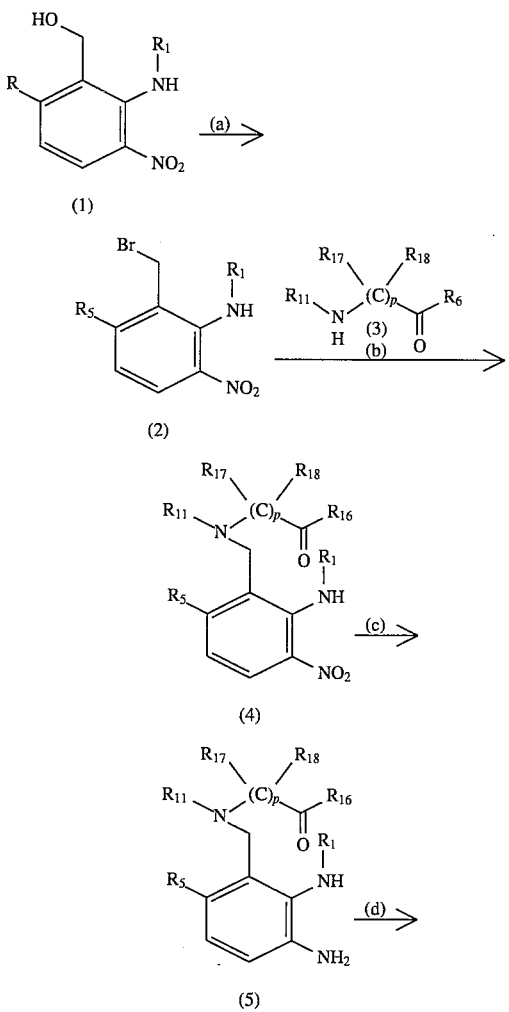

-continued
GENERAL SCHEME II

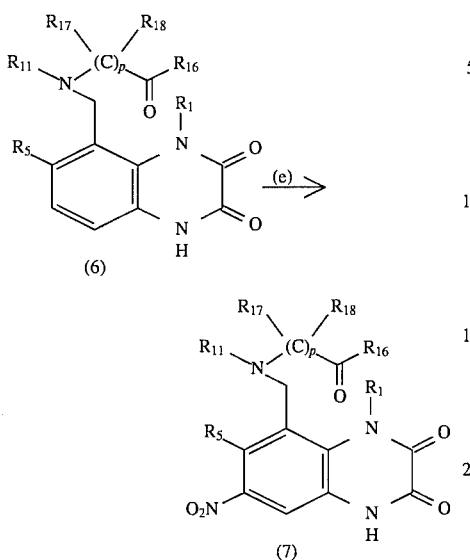

In Scheme III above, step (a) involves the bromination of the benzylic alcohol derivative depicted in formula (1) using brominating agents like phosphoryl bromide or carbon tetrabromide triphenyl phosphine mixture in the presence of an ethereal solvent like diethyl ether at temperatures ranging from 0° C. to room temperature. Reaction is evaporated to give the crude product, which was purified by column chromatography, to give the desired benzyl bromide depicted in formula (2).

Step (b) involves the reaction of the benzyl bromide (2) with the aminoacid derivative depicted in formula (3) in the presence of a base like triethylamine in solvent mixtures like THF and DMF at room temperature. The reaction is stirred for around 8 hours and evaporated to dryness. Product is extracted in a chlorinated solvent like chloroform and washed with water and dried over MgSO$_4$. Crude product is purified by column chromatography over silica gel with eluents as mixtures of solvents like chloroform and methanol.

Step (c) involves the reduction of the nitroaniline derivative depicted in formula (4) via hydrogenation (hydrogen gas around 50 psi) using Ra Ni as the catalyst in a solution of an ether or hydroxylated solvent preferably tetrahydrofuran. Catalyst is filtered off, and the filtrate is evaporated and used in step (d) without further purification.

Step (d) involves reacting o-phenylenediamine derivative depicted in formula (5) with an oxalic acid derivative, preferably dimethyl oxalate in hydroxylated solvent preferably methanol at refluxing temperatures. The reaction mixture is evaporated under reduced pressure, and the solid obtained is triturated with methanol and filtered. The product (6) is dried and used in step (e).

Step (e) involves reacting quinoxaline 2,3-dione derivative depicted in formula (6) with nitrating agent like potassium nitrate in acidic solvent like TFA or H$_2$SO$_4$, preferably H$_2$SO$_4$ at 0°–5° C. Reaction stirred for about 8 hours and poured on ice-water. The dark reaction mixture was filtered, and the filtrate is neutralized with gaseous ammonia. The product (7) obtained is purified by crystallization or column chromatography (SiO$_2$) with varying proportions of CHCl$_3$:MeOH mixtures.

Scheme 3

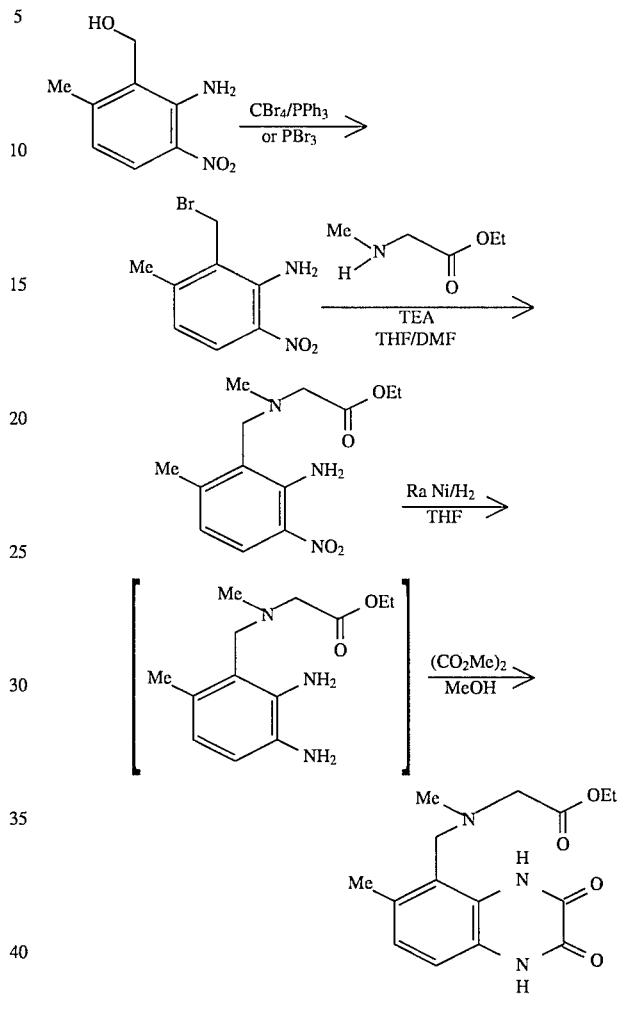

Scheme 3

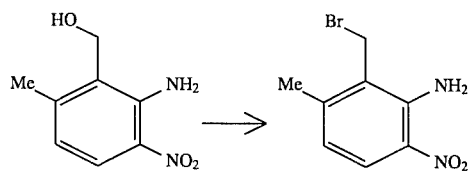

2-Bromomethyl-3-methyl-6-nitro-phenylamine

To a solution of CBr$_4$ (2.18 g, 6.6 mmol) and PPh$_3$ (1.73 g, 6.6 mmol) in anhydrous ether (100 mL), (2-amino-6-methyl-3-nitro-phenyl)-methanol (1.08 g, 5.9 mmol) was added under stirring and nitrogen. The reaction was stopped after monitoring by TLC (SiO$_2$, pet. ether:EtOAc, 1:1). The reaction mixture was filtered and the filtrate evaporated. The dark yellow residue was chromatographed (SiO$_2$, pet. ether:EtOAc, 9:1 to 8:2). Yellow solid, 0.620 g, 43%. H-NMR, CDCl$_3$: 2.38 (s, 3H), 4.49 (s, 2H), 6.45 (bs, 2H), 6.57 (d, 1H, 8.7 Hz), 8.03 (d, 1H, 8.7 Hz).

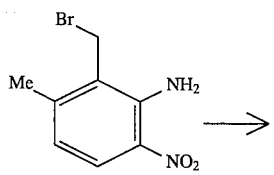

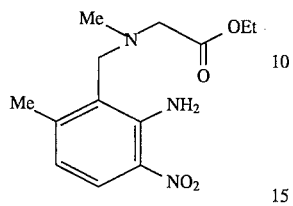

[(2-Amino-6-methyl-3-nitro-benzyl)-methyl-amino]-acetic acid ethyl ester

To a suspension of sarcosine ethyl ester hydrochloride (0.765 g, 5 mmol) in DMF:THF (1:1, 10 mL), triethylamine (1.01 g, 10 mmol) was added under stirring. After 15 minutes, 2-bromomethyl-3-methyl-6-nitro-phenylamine (0.6 g, 2.44 mmol) was added. Reaction mixture stirred at room temperature for 18 hours and evaporated to dryness. Product extracted with $CHCl_3$ (100 mL) and washed with water and dried over $MgSO_4$. Solvent evaporated to give an oil (0.711 g), which was chromatographed ($SiO_2$, pet. ether:EtOAc, 95:5 to 80:20). Orange yellow solid. Yield: 0.530 g, 77%. MS (CI): M+1=282.

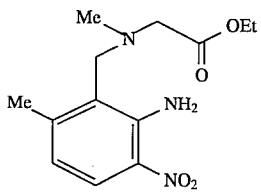

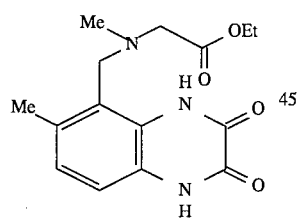

[(6-Methyl-2,3-dioxo-1,2,3,4-tetrahydro-quinoxalin-5-ylm-ethyl)-methyl-amino]-acetic acid ethyl ester A solution of [(2-amino-6-methyl-3-nitro-benzyl)-methyl-amino]-acetic acid ethyl ester (0.49 g) in THF (75 mL) was hydrogenated ($H_2$, 50 psi) over Ra Ni (0.2 g) in a Parr apparatus. The reaction mixture was filtered, and the dark solid (0.500 g) was treated with dimethyl oxalate (0.295 g, 2.5 mmol) in MeOH. The reaction mixture was refluxed for 16 hours and evaporated to dryness. Product was extracted in $CHCl_3$ (100 mL), washed with water and dried ($MgSO_4$). Crude (0.689 g) was chromatographed ($SiO_2$, $CHCl_3$:MeOH, 100 to 95:5) to give yellow solid. Yield: 0.38 g, 62%. MS (CI): M+1=306.

I claim:

1. A compound of Formula I

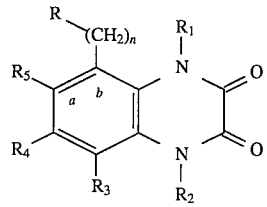

or a pharmaceutically acceptable salt thereof wherein

R is

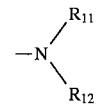

wherein $R_{11}$ is hydrogen, alkyl, or aralkyl, and $R_{12}$ is of the formula

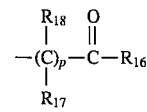

wherein p is an integer of from 1 to 5 and $R_{17}$ and $R_{18}$ are each independently on any carbon in $—(C)_p—$ and wherein $R_{16}$ is hydroxy, alkoxy, $NR_{19}R_{20}$ wherein $R_{19}$ and $R_{20}$ are each independently hydrogen, alkyl, cycloalkyl, or aralkyl, and $R_{17}$ and $R_{18}$ are independently selected from hydrogen, alkyl, aryl, cycloalkyl, heterocycloalkyl, aralkyl, heteroaralkyl, carboxyalkyl, aminoalkyl, thioalkyl, or hydroxyalkyl;

n is an integer of from 1 to 4;

$R_1$ is hydrogen, alkyl, aralkyl, carboxyalkyl, phosphoroalkyl, or phosphonoalkyl;

$R_2$ is hydrogen hydroxy or amino;

$R_3$ and $R_4$ are each independently hydrogen, alkyl, cycloalkyl, alkenyl, halogen, haloalkyl, nitro, cyano, $SO_2CF_3$, $C(O)R_6$ wherein $R_6$ is hydroxy, alkoxy,

alkyl, haloalkyl, aryl, aralkyl, $CH_2SO_2R_6$, $(CH_2)_mCO_2R_9$ wherein $R_9$ is hydrogen, alkyl, aralkyl, or cycloalkyl, $(CH_2)_mCONR_7R_8$, $(CH_2)_mSO_2NR_7R_8$, or $NHCOR_6$ wherein m is an integer of from 0 to 4 and $R_7$ and $R_8$ are each independently selected from hydrogen, alkyl, cycloalkyl, haloalkyl, or aralkyl;

$R_5$ is hydrogen, alkyl, alkenyl, alkynyl, cycloalkyl, halogen, haloalkyl, aryl, heteroaralkyl, aralkyl, heteroaryl, nitro, cyano, $SO_2CF_3$ $C(O)R_6$, $(CH_2)_mCO_2R_9$, $(CH_2)_mCONR_7R_8$, $SONR_7R_8$, or $NHCOR_6$ wherein m is as defined above and $R_7$ and $R_8$ are each independently hydrogen, alkyl, cycloalkyl, or aralkyl; and $R_5$ may be at the b-position and $R—(CH_2)_n—$ at the a-position on the ring.

2. A compound according to claim 1 wherein:

R is

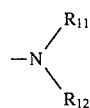

wherein $R_{11}$ is hydrogen, alkyl, or aralkyl, and $R_{12}$ is an amino acid of formula

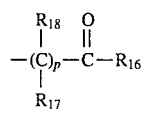

wherein p is an integer of from 1 to 5 and $R_{17}$ and $R_{18}$ are each independently on any carbon in $-(C)_p-$ and wherein $R_{16}$ is hydroxy, alkoxy, $NR_{19}R_{20}$ wherein $R_{19}$ and $R_{20}$ are each independently hydrogen, alkyl, cycloalkyl, or aralkyl, and $R_{17}$ and $R_{18}$ are independently selected from hydrogen, alkyl, aryl, cycloalkyl, heterocycloalkyl, aralkyl, heteroaralkyl, carboxyalkyl, aminoalkyl, thioalkyl, or hydroxyalkyl;

$R_1$ is hydrogen, alkyl, aralkyl, carboxyalkyl, phosphoroalkyl, or phosphonoalkyl;

$R_2$ is hydrogen, hydroxy, or amino;

$R_3$ and $R_4$ are each independently hydrogen, alkyl, cycloalkyl, alkenyl, halogen, haloalkyl, nitro, cyano, $SO_2CF_3$, $C(O)R_6$, $CH_2SO_2R_6$, $(CH_2)_mCO_2R_9$, $(CH_2)_mCONR_7R_8$, $(CH_2)_mSO_2NR_7R_8$ or $NHCOR_6$ wherein m is an integer of from 0 to 4 and $R_6$ is selected from hydrogen, alkyl, cycloalkyl, or aralkyl, and $R_5$ is hydrogen, alkyl, alkenyl, alkynyl, cycloalkyl, halogen, haloalkyl, aryl, aralkyl, heteroaryl, nitro, cyano, $SO_2CF_3$, $C(O)R_6$ wherein $R_6$ is hydroxy, alkoxy,

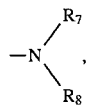

alkyl, haloalkyl, aryl, or aralkyl, $(CH_2)_mCO_2R_9$, $(CH_2)_mCONR_7R_8$, $SONR_9$ $R_{10}$, or $NHCOR_6$ wherein m is as defined above and $R_7$ and $R_8$ are each independently hydrogen, alkyl, cycloalkyl, or aralkyl; and $R_5$ may also be at the b-position and $R-(CH_2)_n-$ at the a-position on the ring.

3. A compound according to claim 2 wherein wherein R is

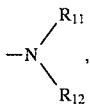

wherein $R_{11}$ is hydrogen or methyl, wherein $R_{12}$ is

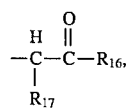

wherein $R_{16}$ is hydroxy, alkoxy, or amine, and $R_{17}$ is hydrogen alkyl, cycloalkyl, heterocycloalkyl, aryl, aralkyl, heteroaralkyl, carboxyalkyl, aminoalkyl, thioalkyl, or hydroxyalkyl;

$R_1$ is hydrogen;

$R_2$ is hydrogen;

$R_3$ and $R_4$ are each independently hydrogen, halogen, or nitro;

$R_5$ is hydrogen, alkyl, or alkenyl.

4. A compound according to claim 1 selected from:
[(7-Bromo-2,3-dioxo-6-vinyl-1,2,3,4-tetrahydro-quinoxalin-5-ylmethyl)-methyl-amino]-acetic acid;
[(7-Bromo-6-ethyl-2,3-dioxo-1,2,3,4-tetrahydro-quinoxalin-5-ylmethyl)-methyl-amino]-acetic acid; and
[(6-Ethyl-7-nitro-2,3-dioxo-1,2,3,4-tetrahydro-quinoxalin-5-ylmethyl)-methyl-amino]-acetic acid ethyl ester.

5. A compound according to claim 1 and named [(6-Ethyl-7-nitro-2,3-dioxo-1,2,3,4-tetrahydro-quinoxalin-5-ylmethyl)-methyl-amino]-acetic acid.

6. A pharmaceutical composition comprising a therapeutically effective amount of a compound according to claim 1 together with a pharmaceutically acceptable carrier in unit dosage form.

7. A method for treating disorders responsive to the blockade of glutamate receptors in a patient suffering therefrom which comprises administering a composition according to claim 1.

8. A method for treating stroke which comprises administering a therapeutically effective amount of a compound according to claim 1 to a patient in need of said treatment.

9. A method for treating cerebral hypoxia/ischemia which comprises administering a therapeutically effective amount of a compound according to claim 1 to a patient in need of said treatment.

10. A method for treating Alzheimer's disease which comprises administering a therapeutically effective amount of a compound according to claim 1 to a patient in need of said treatment.

11. A method for treating Parkinsonism which comprises administering a therapeutically effective amount of a compound according to claim 1 to a patient in need of said treatment.

12. A method for treating Huntington's disease which comprises administering a therapeutically effective amount of a compound according to claim 1 to a patient in need of said treatment.

13. A method for treating disorders responsive to anticonvulsants which comprises administering a therapeutically effective amount of a compound according to claim 1 to a patient in need of said treatment.

14. A compound selected from

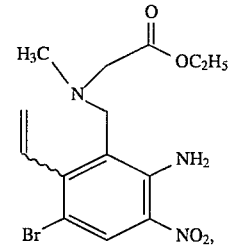

29
-continued
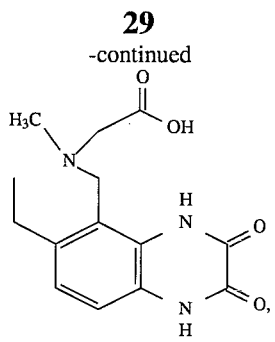
and
30
-continued
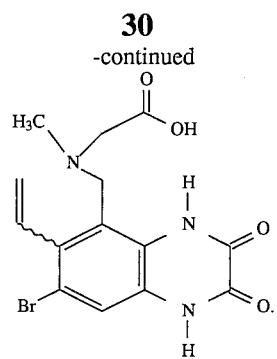
\* \* \* \* \*